United States Patent [19]

Iversen et al.

[11] Patent Number: 4,685,447

[45] Date of Patent: Aug. 11, 1987

[54] TISSUE EXPANDER SYSTEM

[75] Inventors: Alfred A. Iversen; William J. Eastman, both of Hopkins; Allen L. Van Beek, Edina, all of Minn.

[73] Assignee: PMT Corporation, Hopkins, Minn.

[21] Appl. No.: 715,457

[22] Filed: Mar. 25, 1985

[51] Int. Cl.[4] .................... A61B 19/00; A61F 2/02; A61M 29/00
[52] U.S. Cl. ..................... 128/1 R; 128/DIG. 14; 128/DIG. 20; 128/DIG. 21; 604/96; 604/103; 623/8; 623/11
[58] Field of Search ...... 128/1 R, DIG. 14, DIG. 20, 128/DIG. 25; 604/96, 103; 623/11, 12, 7, 8

[56] References Cited

U.S. PATENT DOCUMENTS

| | | | |
|---|---|---|---|
| 2,842,775 | 7/1958 | Pangman | 623/8 |
| 3,528,869 | 9/1970 | Dereniuk | 604/103 X |
| 3,831,583 | 8/1974 | Edmunds, Jr. et al. | 128/1 R |
| 4,190,040 | 2/1980 | Schulte | 623/8 X |
| 4,217,889 | 8/1980 | Radovan et al. | 128/1 R |
| 4,413,359 | 11/1983 | Akiyama et al. | 128/DIG. 14 |
| 4,536,179 | 8/1985 | Anderson et al. | 128/DIG. 14 X |

*Primary Examiner*—Ronald L. Frinks
*Attorney, Agent, or Firm*—Hugh D. Jaeger

[57] ABSTRACT

Tissue expander system including a tissue expander, an injection port, and a tube connecting the tissue expander to the injection port. The tissue expander is of a one piece molded body of a pancake to waffle like configuration. Within the one piece molded body is a member of non-stick material of a slightly smaller geometrical shape similar to that of the one piece molded body. A self-sealing valve member closes off the tube in the tissue expander after injection of a solution for expanding the tissue expander. A Dacron mesh can be embedded in members of the one piece body providing for directional expansion of the tissue expander. In an alternative embodiment, Dacron mesh can be provided in both the upper and lower members of the one piece body. An accordion configured perimeter also provides for upward directional expansion. The tissue expanders can assume any geometrical configuration, whether it be square, rectangular, circular, oval, or kidney shaped. The tissue expander can also be a small enough size for hands and toes, a miniature size for use on the face, or a large size for use on the chest or other body area. A self-sealing injection port can be domed or cylindrical, and includes a stainless steel bottom, as well as a Dacron mesh impregnated silicone top. The stainless steel bottom provides for limiting injection needle penetration and for injection port location during X-ray procedure.

29 Claims, 16 Drawing Figures

TISSUE EXPANDER SYSTEM

BACKGROUND OF THE INVENTION

1. Field of the Invention

The present invention pertains to plastic and reconstructive surgery, and more particularly, pertains to a tissue expander system for transmitting fluid to a tissue expander for expanding tissue typically adjacent to a reconstructive site where extra tissue is required for repair. An example is growing tissue around and about scar tissue where the scar tissue is subsequently removed, and the grown tissue is stretched and pulled over the previous scar tissue area.

2. Description of the Prior Art

The prior art tissue expanders include a balloon-type reservoir with tubing and injection ports. The prior art tissue expanders are not one continuous molded piece, and have been glued together whereby the glue subsequently breaks at a seam, thereby leaking fluid out of the tissue expander. Also, the prior art tissue expanders are similar to big balloons, which upon insertion, wrinkle and are also extremely hard to slip under the skin. Also, the prior art devices are not directional in expansion, but expanded out in a balloon type fashion with a fat center and narrow on the sides.

A representative prior art patent in U.S. Pat. No. 4,217,889 entitled "Flap Development Device and Method or Progressively Increasing Skin Area", issued Aug. 19, 1980, to Radovan et al. Another representative patent is U.S. Pat. No. 4,157,085 entitled "Surgically Implantable Tissue Expanding Device and the Method of its Use", issued on June 5, 1979, to Austad. A representative patent of a prior art injection port is U.S. Pat. No. 4,190,040, entitled "Resealable Puncture Housing for Surgical Implantation", issued Feb. 26, 1980, to Schulte. The above three patents are representative of the state of the prior art devices.

The present invention overcomes the disadvantages of the prior art by providing a one piece molded tissue expander for a tissue expander system, the tissue expander expanding along a directional axis. An injection port includes a metal plate for needle insertion which limits pentration. The metal plate also locates the injection port during X-ray procedure. The injection port also includes a reinforced self-sealing dome for the insertion of a needle.

SUMMARY OF THE INVENTION

The general purpose of the present invention is a tissue expander system including a tissue expander which provides a small, flat, pancake-waffle member which can slide under a slit in the skin with minimal trauma to the existing tissue. The tissue expander is self-sealing at the reservoir end by using an internal member of low coefficient friction non-stick material, which acts as a valve, and also acts to keep the tube linking the injection port and the expander free and clear of silicone, or like material, during the molding process. The tissue expander section is directional in axial expansion; thus, allowing the surgeon to provide ultimate directional control for tissue growth. The injection port includes a stainless steel circular member which can be readily located by feel or by X-ray due to the metal circular member embedded in the silicone dacron silicone matrix. The metal member also acts as a needle stop during injection of a saline or like solution.

According to one embodiment of the present invention, there is provided a tissue expander system including a one piece molded tissue expander including a cavity therein and a tube connected thereto, at least one member of non-stick material freely supported in the cavity is integral to the tissue expander about the tube for valving fluid into the tissue expander, and an injection port including a stainless steel member providing for control of needle insertion, as well as X-ray location. Two members of non-stick material can be provided, one member about the tube input for valving of fluid during expansion and the other member between surfaces of the molded tissue expander providing for expansion of the surfaces with respect to each other. The tissue expander is directional in expansion, and can include at least one surface member which includes a Dacron (trademark of E. I. DuPont Co.) a name for polyethylene terephthalate mesh controlling direction of expansion. The tissue expander can also include accordion-like perimeter sides providing for absolute directional movement during expansion in an upward direction.

One significant aspect and feature of the present invention is a one piece molded tissue expander which is a flat "pancake" shape reducing trauma to the tissue and skin during entry of the tissue expander.

Another significant aspect and feature of the present invention is a one piece molded tissue expander, including a piece of Teflon (Trademark of E. I. DuPont Co.) a name for polytetrafluoroethylene (PTFE) or other like non-stick fluorocarbon material, which provides for non-sticking surfaces during expansion based on the flat one piece molded shape. One surface can also includ Dacron mesh providing for substantially minimal expansion across that particular surface, while the other surface is above to expand freely as required.

A further significant aspect and feature of the present invention is a valve of non-stick fluorocarbon material including a self-sealing member across the tube embedded in the tissue expander providing for passage of a solution in only one direction.

An additional significant aspect and feature is a metal member in the injection port which eliminates bottom side needle puncture during needle insertion and also provides for location during X-ray procedure.

Another additional significant aspect and feature is a prestressed member in a dome of the injection port which aids in sealing of the needle puncture.

Having thus described embodiments of the present invention, it is the principal object hereof to provide a tissue expander system including a one piece molded tissue expander with a valved tube and a member of non-stick material between the upper and lower surface of the tissue expander; and, including an injection port with a metal member providing for location during X-ray procedures, as well as preventing bottom side needle punctures during insertion of a needle for filling of the system with a saline or like solution for expansion of the tissue expander.

One object of the present invention is a tissue expander system which is a flat, pancake-waffle shape which easily slides in between the skin and flesh during entry, reducing trauma to the surrounding tissue. A member of non-stick material is between the surfaces of the tissue expander providing for non-sticking of surfaces during expansion.

Another object of the present invention is a tissue expander which is a one piece molded integral unit providing for directional expansion over a geometrical surface area as predetermined. One surface of the tissue expander can be reinforced with Dacron mesh providing for expansion of the opposing surface.

A further object of the present invention is a tissue expander which includes a port which has an X-ray opaque metal strip allowing for determination of the port entry location for the needle. Also, the X-ray opaque metal strip prevents bottom side needle puncture during needle insetion to insure proper solution injection with the injection port.

An additional object of the present invention is a tissue expander which includes a self-sealing port by a flap of non-stick material for a fluid introduction tube so that the fluid cannot depressurize back through the tube of the tissue expander.

DESCRIPTION OF THE PREFERRED EMBODIMENTS

Figure 1:
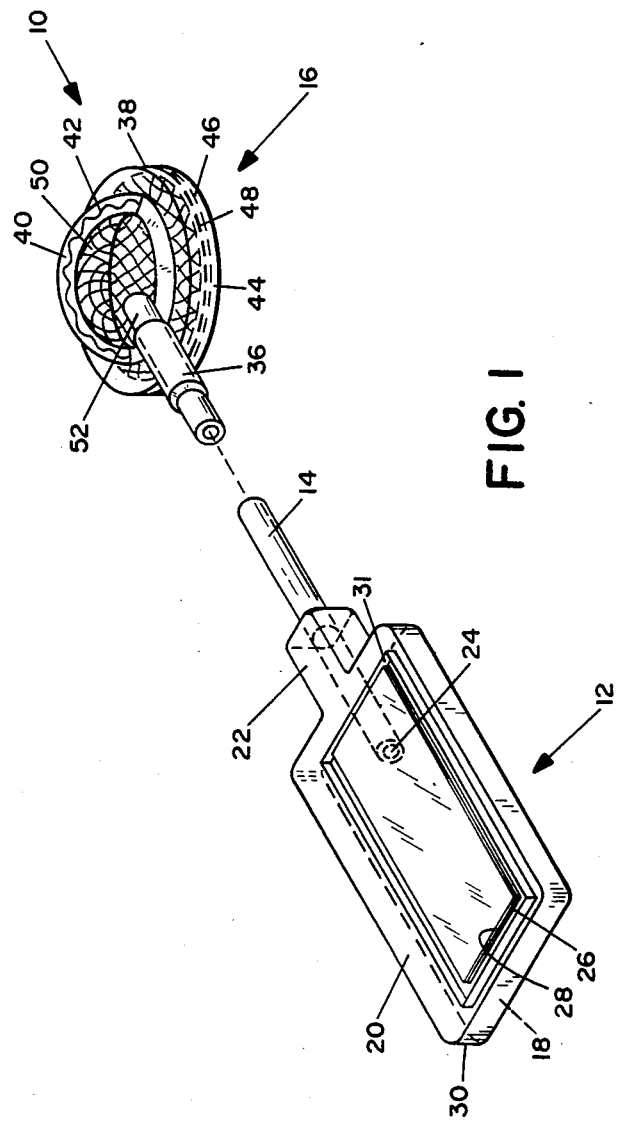
FIG. 1 illustrates a perspective view of a tissue expand system including a tissue expander, an injection port, and a connecting tube.

FIG. 1 illustrates a perspective view of a tissue expander system 10 including a tissue expander 12, a connecting tube 14 and an injection port 16. The tissue expander 12 is molded into a one piece of silicone rubber, polyurethane, or other like medical grade polymer or like expandable and stretchable material. The tissue expander 12 includes a bottom layer 18, a top layer 20, and a housing 22 for the tube 14. The tube 14 has a substantially flat tube end 24, and is encompassed by a bottom non-stick fluorocarbon material layer 26 and a like non-stick fluorocarbon material layer 28, the layers surrounding and encompassing the tube end 24. Any suitable low coefficient of friction nonstick material can be utilized including fluorocarbons. The layers 26 and 28 are of a slightly smaller surface area than the top and bottom silicon layers 18 and 20. The layer or layers of non-stick material provides for inherent separation of the top layer from the bottom layer as the non-stick material is inherently free floating in the internal cavity between the layers and up to and adjacent to the edge. The non-stick material, in the alternative, could also be secured at one or more points to the edge. The edge 30 of the tissue expander is molded smooth to layers 18 and 20, and does not have any seams to pull apart under pressure. The edge 30 along with layers 18 and 20 forms an internal cavity 31 which increases an internal volume as later described. The tube 14 connects between the housing 22 and the injection port 16. The injection port includes a silicone housing 36 for supporting the tube 14 and is secured about a smooth molded edge 38. A self-sealing silicone dome 40, including integral Dacron support mesh 42 therein, is molded to the edge 38. The injection dome 40 can be of prestressed silicone which aids in sealing of the needle puncture. For instance, top and bottom layers 40 can be pre-molded silicone inserts where there is shrinkage of inner and outer silicone layers during molding which places compressive prestress on a center member 42 whether that member is Dacron reinforced or is of a different durometer. Further, the silicone matrix can be reinforced such as by Dacron mesh including reinforcement of the top and bottom layers while the prestressed center layer is not Dacron reinforced. A silicone base 44 supports a Dacron base mesh 46 and a stainless steel, or other like metal disk 48. The space between the stainless steel disk 48 and the silicone dome 40 with the Dacron support mesh 42, provides a reinforced cavity 50 for accepting and containing fluid, such as saline solution, during filling of the tissue expander reservoir to expand the tissue expander 12. While the figure illustrates two layers of non-stick material, the tissue expander can function with only one layer of non-stick material where the material acts as a valving flap over the tube end and also provides for separation of the two layers 18 and 20. A particular embodiment would be a micro size tissue expander.

Figure 2:
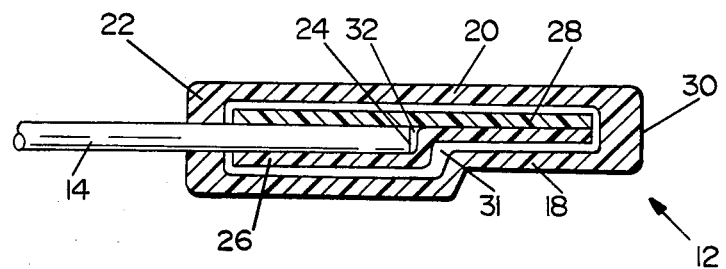
FIG. 2 illustrates a cross sectional view of the tissue expander.

FIG. 2 illustrates a cross-sectional view of the tissue expander 12 of FIG. 1, particularly illustrating the proximity space 32 of the lower of non-stick layers 26 and 28 to the flat tube end 24. Also, the layers 26 and 28 overlap the tube end and extend further back about the tube. All other numerals correspond to those elements previously described. The layers 26 and 28 also protect the tube end 24 during molding so that silicone does not flow back into the tube 24.

Figure 3:
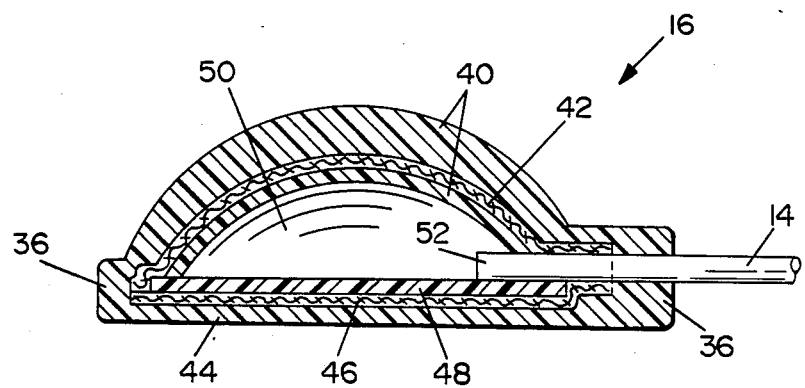
FIG. 3 illustrates a cross sectional view of the injection port.

FIG. 3 illustrates a side view of the injection port 16 where all numerals correspond to those elements previously described. The tube end 52 is free and clear in the cavity 50.

MODE OF OPERATION

A predetermined amount of fluid, such as a saline or other solutions, is injected into the injection port via a syringe or other fluid injection system passed through the skin. A fluid injection system can meter in precise amounts of fluid and sense back pressure during fluid metering. Of course, the tissue expander 12 and injection port 16 have already been placed into an individual under the epidermis and above the flesh. As the tissue expander is inflated, over a period of typically several weeks, the tissue enlarges or grows to accommodate the enlarging tissue expander. The tissue grows to a size predetermined by the surgeon-physician.

Figure 4:
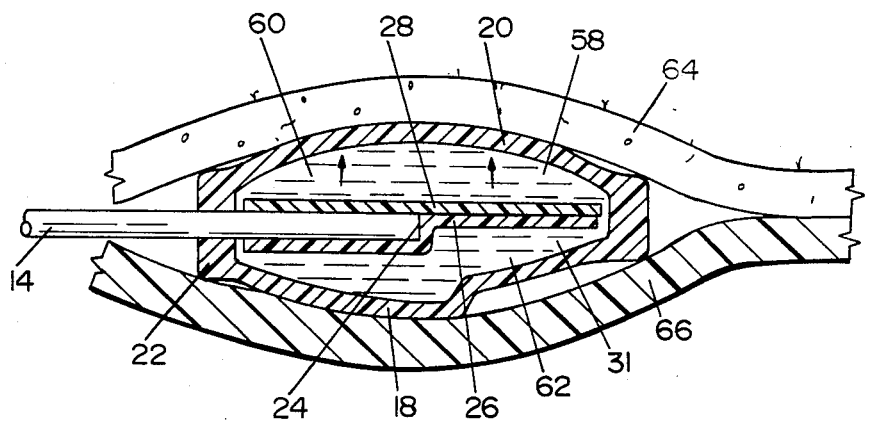
FIG. 4 illustrates a cross sectional view of a slightly expanded tissue expander inserted under the epidermis.

FIG. 4 illustrates the tissue expander slightly expanded with a saline solution 58 and areas 60 and 62 filled by the solution. The non-stick members 26 and 28 have a two fold purpose. The first purpose is acting as a back flow valve in that the pressure of the solution acting against the non-stick material and the flat end of the tube 24 provides that no liquid can flow in the opposite direction back towards the injection port. Second, the non-stick members provide that the silicone members 18 and 20 will quickly, easily, and properly separate from the each other for expansion. In this particular example, the tissue expander expands more towards the top layer 20 than towards the bottom layer 18, thereby pushing the epidermis 64 upwards away from the flesh 66.

ALTERNATIVE EMBODIMENT OF INJECTION PORT

Figure 5:
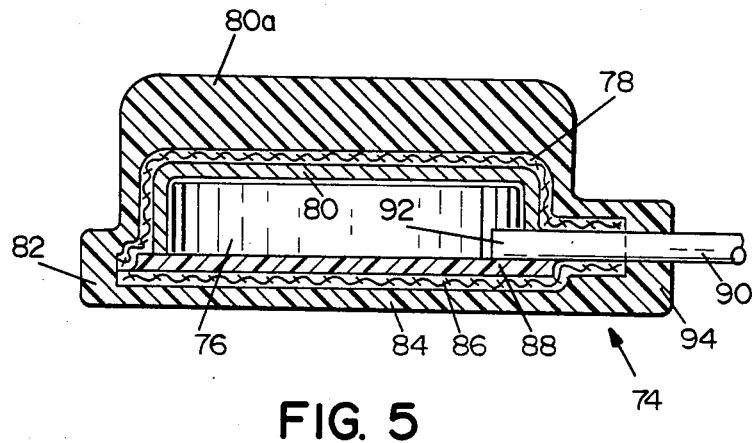
FIG. 5 illustrates an alternative embodiment of a cross sectional view of a cylindrical injection port.

FIG. 5 illustrates a cross-section view of an alternative embodiment of a cylindrical injection port 74 including a cylindrical cavity member 76. A Dacron mesh 78 is contained within an upper round silicone rubber rectangular cavity member 80. Layer member 80a is of a thickness of a greater dimension than member 80, thereby forming a sandwiched layer. The members 76-80 are fused together at fused edge 82. A lower silicone base 84 supports a Dacron mesh 86 and a stainless steel circular member 88. A tube 90, including an end 92, extends in through silicone housing 94. The injection port 74 can likewise include a center prestressed member or the like as previously discussed for FIGS. 1-4.

Figure 6:
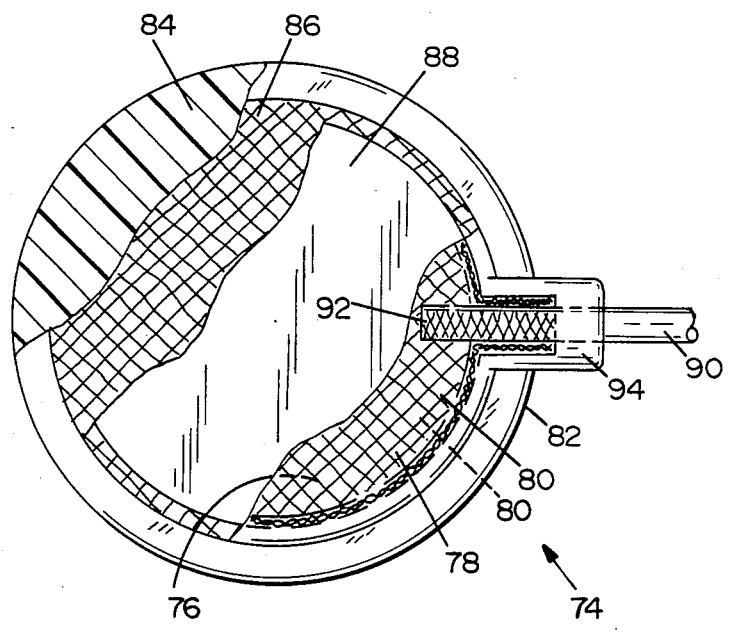
FIG. 6 illustrates a top cutaway view of the injection port of FIG. 5.

FIG. 6 illustrates a top view of FIG. 5 where all numerals correspond to those elements previously described. Particularly, the cylindrical shape of the injection port is illustrated.

ALTERNATIVE EMBODIMENTS OF TISSUE EXPANDER

Figure 7:
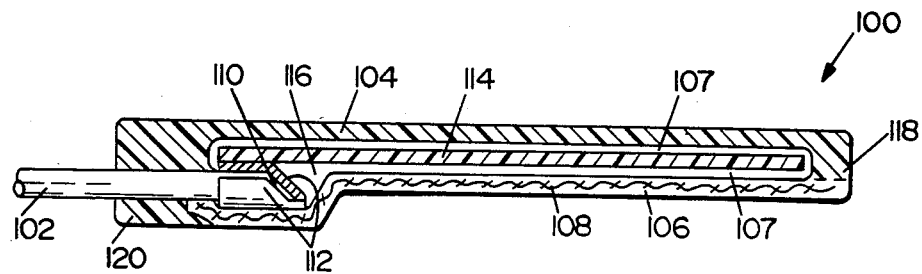
FIG. 7 illustrates an alternate cross section embodiment of a tissue expander.

FIG. 7 illustrates an alternative embodiment of a tissue expander 100, including a tube 102, an upper silicone layer 104, and a lower silicone layer 106, where the lower silicone layer supports a dacron mesh 108. A cavity 107 is formed between layers 104 and 106 and edge 118. The tube 102 has an angled end 110. A piece of non-stick material such as Teflon, or like material, 112 press fits around the bottom portion of the end of the tube and then folds back across the angled end 110 to function as a valve. A non-stick material member separator 114 positions through the inner surface area of the tissue expander 100. A small area 116 is inherently provided for entry of the fluid, as well as movement of the non-stick material valve flap 112. The entire assembly is molded about an edge 118, and includes a housing portion 120 for supporting the tube 102 about the layers 104 and 106.

Figure 8:
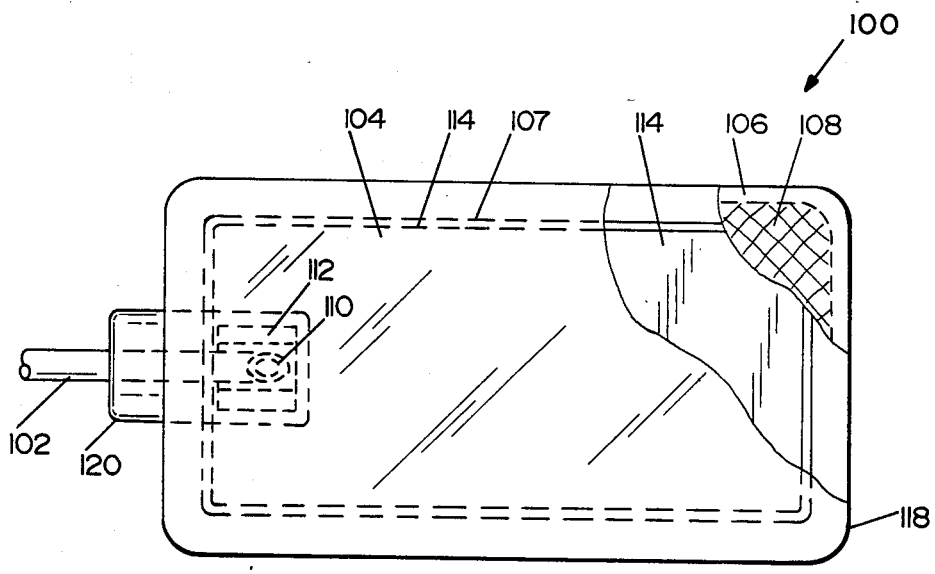
FIG. 8 illustrates a top cutaway view of the tissue expander of FIG. 7.

FIG. 8 illustrates a top view of the tissue expander 100 of FIG. 7 where all numerals correspond to those elements previously described. The surface area of the Teflon separator 114 is slightly smaller than the overall surface area, and lies within the cavity 107 formed by the inner perimeter of edge 118 and the inner surfaces of members 104 and 106.

MODE OF OPERATION OF ALTERNATIVE EMBODIMENT OF TISSUE EXPANDER

Figure 9:
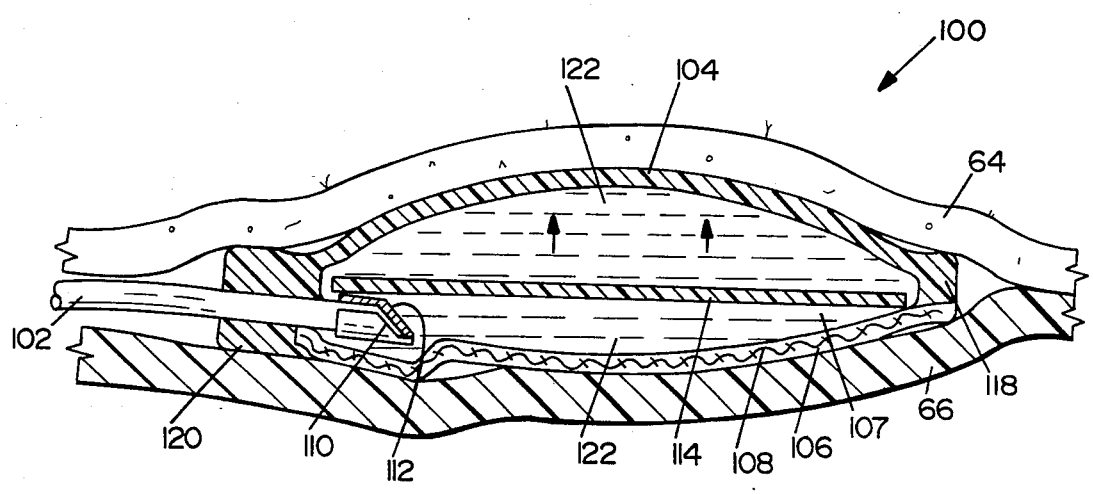
FIG. 9 illustrates a cross sectional view of the FIG. 7 alternate embodiment tissue expander inserted beneath the epidermis.

FIG. 9 illustrates the tissue expander 100 in an activated condition, inlcuding saline solution 122 within the tissue expander. The bottom layer 106, supporting the Dacron mesh 108 within, provides for very minimal expansion downwardly, while the upper silicone layer 104 provides for an optimized expansion upwardly, providing directional control of the expansion. The back pressure of the fluid against the flap 112 at the angle tube end 110 provides a valving action preventing back flow of the fluid 122. The non-stick material 114 allows for easy and rapid separation and expansion of the top and bottom surfaces.

SECOND ALTERNATIVE EMBODIMENT OF THE TISSUE EXPANDER

Figure 10:
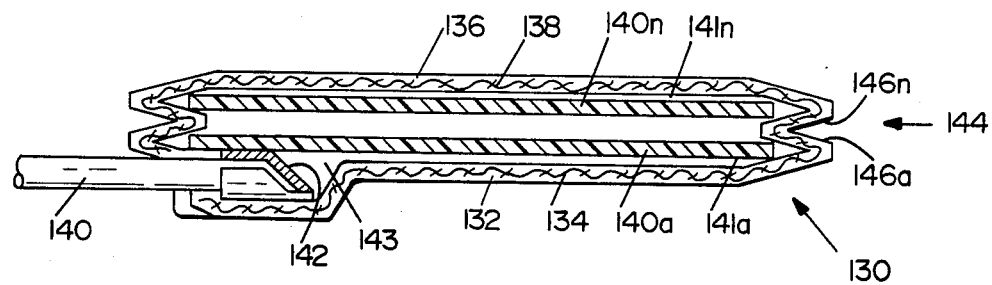
FIG. 10 illustrates a second alternate embodiment cross section of a tissue expander using accordion walls.

FIG. 10 illustrates a tissue expander 130, including a lower silicone member 132 with a Dacron mesh 134 embedded therein, an upper silicone member 136 with a Dacron mesh 138 embedded therein, and a inlet tube 140 including a non-stick sealing flap 142 extending into the inherently formed cavity 143. Inner non-stick layers 140a-140n position in cavities 141a-141n between the silicone layers 132 and 136 and sides providing for ease of active separation as now described. An accordion side member 144, including a plurality of accordion members 146a-146n, are molded about the bottom and top layers 132 and 136 and mid layers accordingly. The tissue expander expands in an axial upward direction the travel of which is based upon the number of accordion sections between the two layers 132 and 136.

Figure 11:
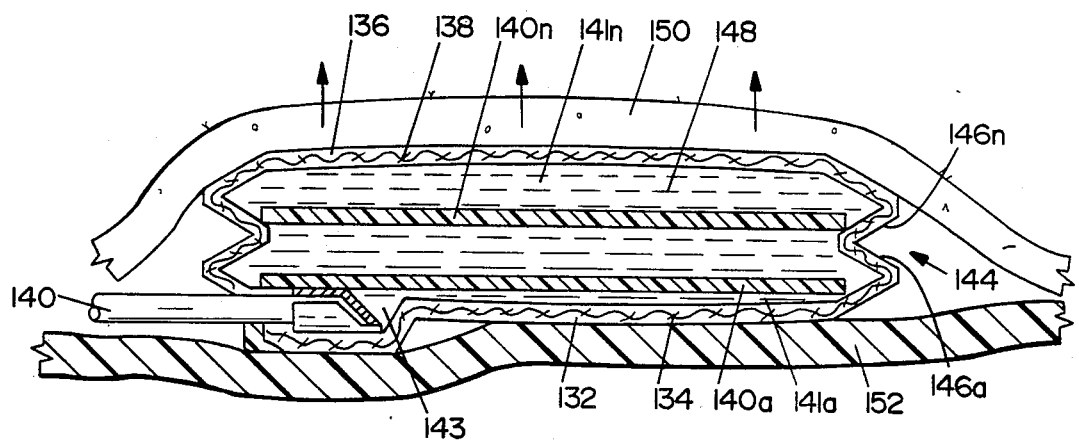
FIG. 11 illustrates a cross sectional view of the tissue expander of FIG. 10 inserted beneath the epidermis.

FIG. 11 illustrates expanded cross section view of FIG. 10 where all numerals correspond to those element previously described. Particularly illustrated are the expanded state accordion sections with saline solution 148 contained therein, between the epidermis 150 and the flesh 152.

Figure 12:
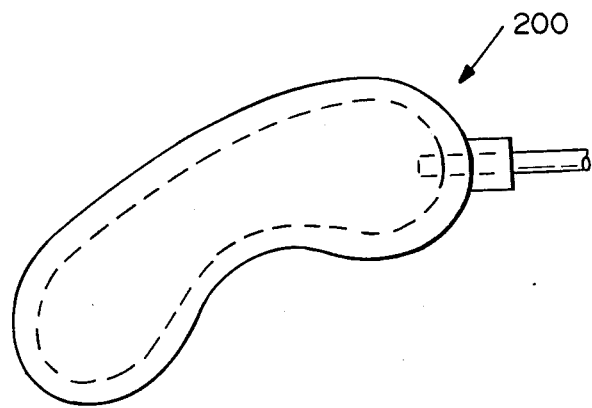
FIG. 12 illustrates an alternate top view embodiment of a kidney shaped tissue expander.
Figure 13:
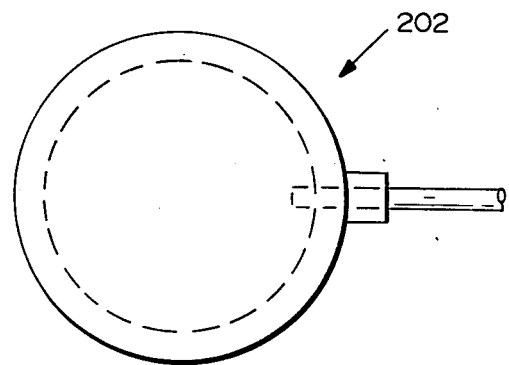
FIG. 13 illustrates an alternate top view embodiment of a round shaped tissue expander.
Figure 14:
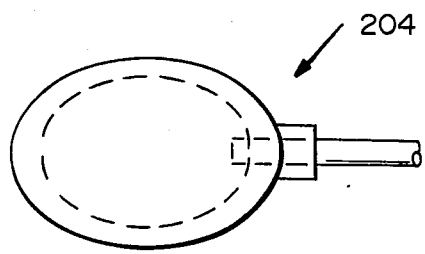
FIG. 14 illustrates an alternate top view embodiment of an oval shaped tissue expander.
Figure 15:
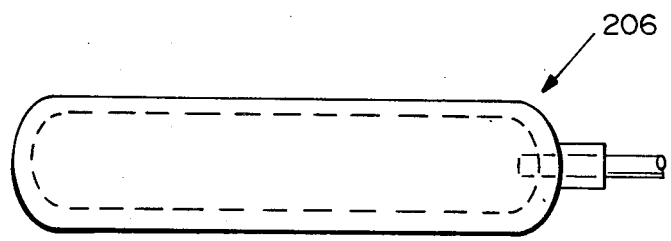
FIG. 15 illustrates an alternate top view embodiment of an oblong shaped tissue expander; and, FIG. 16 illustrates an alternate top view embodiment of a donut shaped tissue expander.
Figure 16:
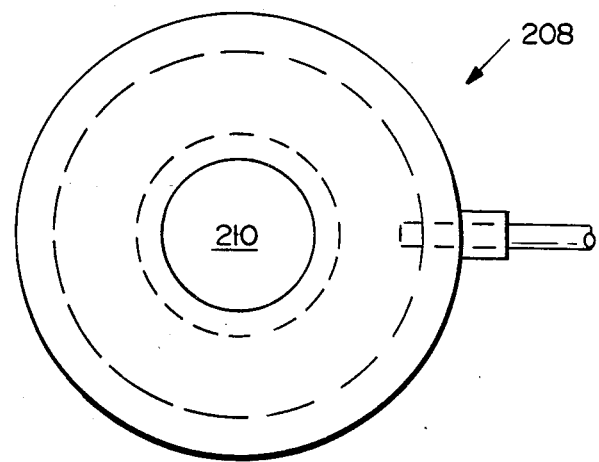

FIGS. 12-16 illustrate top views of additional alternative embodiments of tissue expanders, where the surface area of the geometrical shape can be predetermined accordingly. For example, FIG. 12 illustrates a kidney shaped tissue expander 200, FIG. 13 illustrates a round tissue expander 202, FIG. 14 illustrates an oval tissue expander 204, FIG. 15 illustrates and oblong tissue expander 206, and FIG. 16 illustrates a top view of a donut tissue expander 208 with a hole 210 in the center of the donut. Any geometrical configuration can be utilized with any shape hole in the tissue expander as so desired. The surface area of the tissue expander can assume any predetermined geometrical shape as so desired, as well as the internal member of non-stick material.

The teachings of the present invention can be expanded to any type of a medical appliance device where there are sheets of expandable material, such as silicone rubber, polyurethane, or the like, which require separation or continued separation for whatever reasons, whereupon a layer of non-stick material, such as Teflon or the like, would be inserted therebetween. Another particular example would be an expandable arterial catheter, such as the dilatation balloon catheters. Teflon could be utilized in dilatation balloons when inflated in a stenosis. The use of the non-stick material assures that the layers will not become joined together, such as through compression or for whatever other reasons; and further assures that the layers will rapidly expand upon the introduction of a fluid, whether the fluid be a liquid or air. The principal is that the non-stick material is releasable between the two layers providing for rapid expansion of the layers and so the layers do not stick to each other. The teachings of the present invention are not only applicable to tissue expanders, but also to surgical balloons, such as extrusion catheters or other surgical appliances.

We claim:
1. Tissue expander for insertion between skin and flesh comprising:
   a. one piece molded member of an and a finite thickness and assuming a predetermined geometrical shape, said member including a lower surface and an upper surface with a molded edge formed by said surfaces, and an internal cavity therein;
   b. tube means secured to and extending partially into said cavity providing for fluid to pass into said member; and
   c. at least one sheet of non-stick PTFE material positioned between said upper and lower surface assuming said geometrical shape, and adjacent to an inner portion of said edge.
2. Tissue expander of claim 1 comprising at least two sheets of non-stick material between said surfaces, said tube means extending in between said two sheets.
3. Tissue expander of claim 2 wherein each of said sheets of material.
4. Tissue expander of claim 1 comprising a valve means at said inner end of said tube means.
5. Tissue expander of claim 4 wherein said valve means comprises a section of said non-stick material over an end of said tube.
6. Tissue expander of claim 1 wherein said lower surface includes a mesh disposed within said lower surface.
7. Tissue expander of claim 1 wherein said edge includes accordion expansion means providing for directional expansion.
8. Tissue expander of claim 1 wherein said lower and upper surfaces include a mesh disposed with said lower and upper surfaces.
9. Tissue expander of claim 1 wherein said geometrical shape is square.
10. Tissue expander of claim 1 wherein said geometrical shape is rectangular.
11. Tissue expander of claim 1 wherein said geometrical shape is oval.
12. Tissue expander of claim 1 wherein said geometrical shape is kidney shaped.
13. Tissue expander of claim 1 wherein said geometrical shape is a donut.
14. Tissue expander of claim 1 wherein said geometrical shape is oblong.
15. Tissue expander of claim 1 wherein said geometrical shape is circular.
16. Tissue expander of claim 1 comprising injection port means connected to said tube means for passing of fluid to said member.
17. Tissue expander of claim 16 wherein said injection port includes a raised dome member.
18. Tissue expander of claim 17 wherein said dome member includes a mesh disposed with said dome member.
19. Tissue expander comprising:
   a. one piece molded silicone rubber member of a finite thickness and of a predetermined geometrical shape, said member including a lower surface and an upper surface, a molded edge formed at a junction of said surfaces, and a cavity formed therein;
   b. tube means extending into said cavity at said edge providing for fluid to pass into said member; and,
   c. two sheets of non-stick PTFE material between said surfaces and an end of said tube, said material of a smaller surface area than that of said geometrical shape of said surfaces.
20. Tissue expander comprising:
   a. one piece molded member of a finite thickness and of a predetermined geometrical shape, said member including a lower surface and an upper surface, a molded edge formed at a junction of said surfaces, and a cavity formed therein;
   b. tube means extending into said member at said edge providing for fluid to pass into said member including a valve means for checking fluid flow; and,
   c. one sheet of non-stick PTFE material between said surfaces and an end of said tube, said material of a smaller surface area than that of said geometrical shape of said surfaces.
21. Tissue expander of claim 20 including at least one surface with an impregnated polyethylene terephthalate mesh.
22. Tissue expander of claim 20 wherein said valve means comprises a flap of said material about said tube means.
23. Tissue expander of claim 22 wherein said edge includes an accordion expansion means.
24. Tissue expander of claim 23 wherein at least one of said surfaces includes a polyethylene terephthalate mesh.
25. Tissue expander of claim 20 wherein said one piece molded member is silicone rubber.
26. Tissue expander of claim 20 including a dome injection port means connected to said tube means.
27. Tissue expander of claim 26 wherein a metal base is provided in said injection port means.
28. Tissue expander of claim 26 comprising a mesh embedded in said dome.
29. Tissue expander of claim 26 wherein said injection port is a one piece molded assembly.

* * * * *